(12) United States Patent
Rothstein et al.

(10) Patent No.: US 7,722,632 B2
(45) Date of Patent: May 25, 2010

(54) SURGICAL SUTURE HOLDING DEVICE

(75) Inventors: Paul T. Rothstein, Maple Grove, MN (US); Paul Pignato, Stacy, MN (US); Thomas Daigle, Corcoran, MN (US); Jack Goodman, Ann Arbor, MI (US)

(73) Assignee: Medtronic, Inc., Minneapolis, MN (US)

( * ) Notice: Subject to any disclaimer, the term of this patent is extended or adjusted under 35 U.S.C. 154(b) by 1693 days.

(21) Appl. No.: 10/435,236

(22) Filed: May 9, 2003

(65) Prior Publication Data

US 2004/0225302 A1    Nov. 11, 2004

(51) Int. Cl.
*A61B 17/04*    (2006.01)
(52) U.S. Cl. ................................................ 606/148
(58) Field of Classification Search .............. 606/148, 606/232, 233; 600/201
See application file for complete search history.

(56) References Cited

U.S. PATENT DOCUMENTS

| | | | | |
|---|---|---|---|---|
| 1,243,105 A | * | 10/1917 | Richardson | 24/134 R |
| 2,190,661 A | * | 2/1940 | Hauer | 70/49 |
| 2,315,196 A | * | 3/1943 | Gallione | 248/499 |
| 3,046,929 A | * | 7/1962 | Piver | 114/218 |
| 3,204,311 A | * | 9/1965 | Laviano | 188/65.1 |
| 3,819,039 A | * | 6/1974 | Erickson | 206/388 |
| 4,097,023 A | * | 6/1978 | Muller | 254/391 |
| 4,185,636 A | | 1/1980 | Gabbay et al. | |
| 4,492,229 A | | 1/1985 | Grunwald | |
| 4,766,835 A | * | 8/1988 | Randall et al. | 114/218 |
| 4,899,423 A | | 2/1990 | Randall | |
| 4,956,897 A | * | 9/1990 | Speedie | 24/134 P |
| 5,070,805 A | * | 12/1991 | Plante | 114/218 |
| 5,078,731 A | | 1/1992 | Hayhurst | |
| 5,207,703 A | | 5/1993 | Jain | |
| 5,409,499 A | | 4/1995 | Yi | |
| 5,474,572 A | * | 12/1995 | Hayhurst | 606/232 |
| 5,534,008 A | * | 7/1996 | Acksel | 606/148 |
| 5,548,873 A | * | 8/1996 | Macias | 24/134 R |
| 5,852,853 A | * | 12/1998 | Pennoyer, Jr. | 24/134 P |
| 5,871,489 A | | 2/1999 | Ovil | |
| 5,911,728 A | * | 6/1999 | Sepetka et al. | 606/151 |
| 6,066,160 A | * | 5/2000 | Colvin et al. | 606/232 |
| 6,077,221 A | | 6/2000 | Fowler, Jr. | |
| 6,099,468 A | | 8/2000 | Santilli et al. | |

(Continued)

OTHER PUBLICATIONS

Medtronic, Inc., product brochure entitled "OCTOBASE™ Retractor System"; © Medtronic, Inc. 2000; 4 pgs.

*Primary Examiner*—Todd E Manahan
*Assistant Examiner*—Michael G Mendoza
(74) *Attorney, Agent, or Firm*—Mike Jaro; Jeffrey J. Hohenshell

(57) ABSTRACT

A device for holding a surgical suture including a base, a guide body, a cam body, a bearing member, and a spring member. The base has a top side, a front edge, and a back edge. The guide body projects from the top side of the base and defines a guide face having an entrance side and an exit side. The entrance side is adjacent the front edge and the exit side is adjacent the back edge. The cam body is pivotally mounted to the top side and forms a toothed surface positioned to selectively secure a surgical suture against the guide face. The spring member is positioned between the cam body and the bearing member, biasing the toothed surface toward the guide face.

34 Claims, 10 Drawing Sheets

U.S. PATENT DOCUMENTS

| | | |
|---|---|---|
| 6,190,312 B1 | 2/2001 | Fowler, Jr. |
| 6,213,940 B1 | 4/2001 | Sherts et al. |
| 6,264,605 B1 * | 7/2001 | Scirica et al. ............... 600/227 |
| 6,290,644 B1 * | 9/2001 | Green et al. ................ 600/235 |
| 6,331,157 B2 | 12/2001 | Hancock |
| 6,416,469 B1 * | 7/2002 | Phung et al. ................ 600/232 |
| 6,450,207 B2 | 9/2002 | Villatte et al. |
| 6,468,207 B1 | 10/2002 | Fowler, Jr. |
| 6,547,725 B1 * | 4/2003 | Paolitto et al. .............. 600/201 |
| 6,695,868 B2 * | 2/2004 | Looney et al. .............. 606/232 |
| 2002/0035371 A1 * | 3/2002 | Westhaver et al. .......... 606/148 |

* cited by examiner

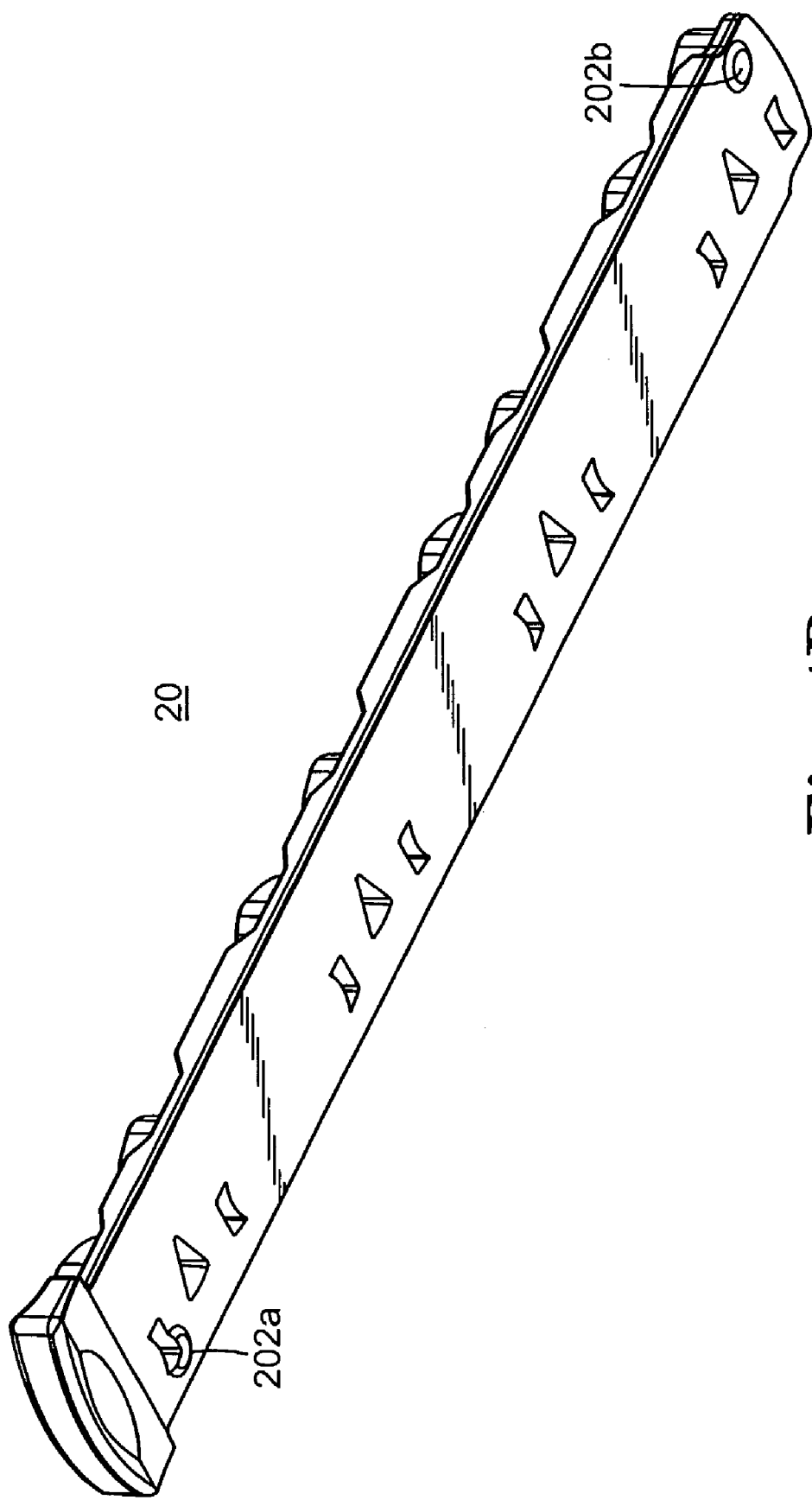

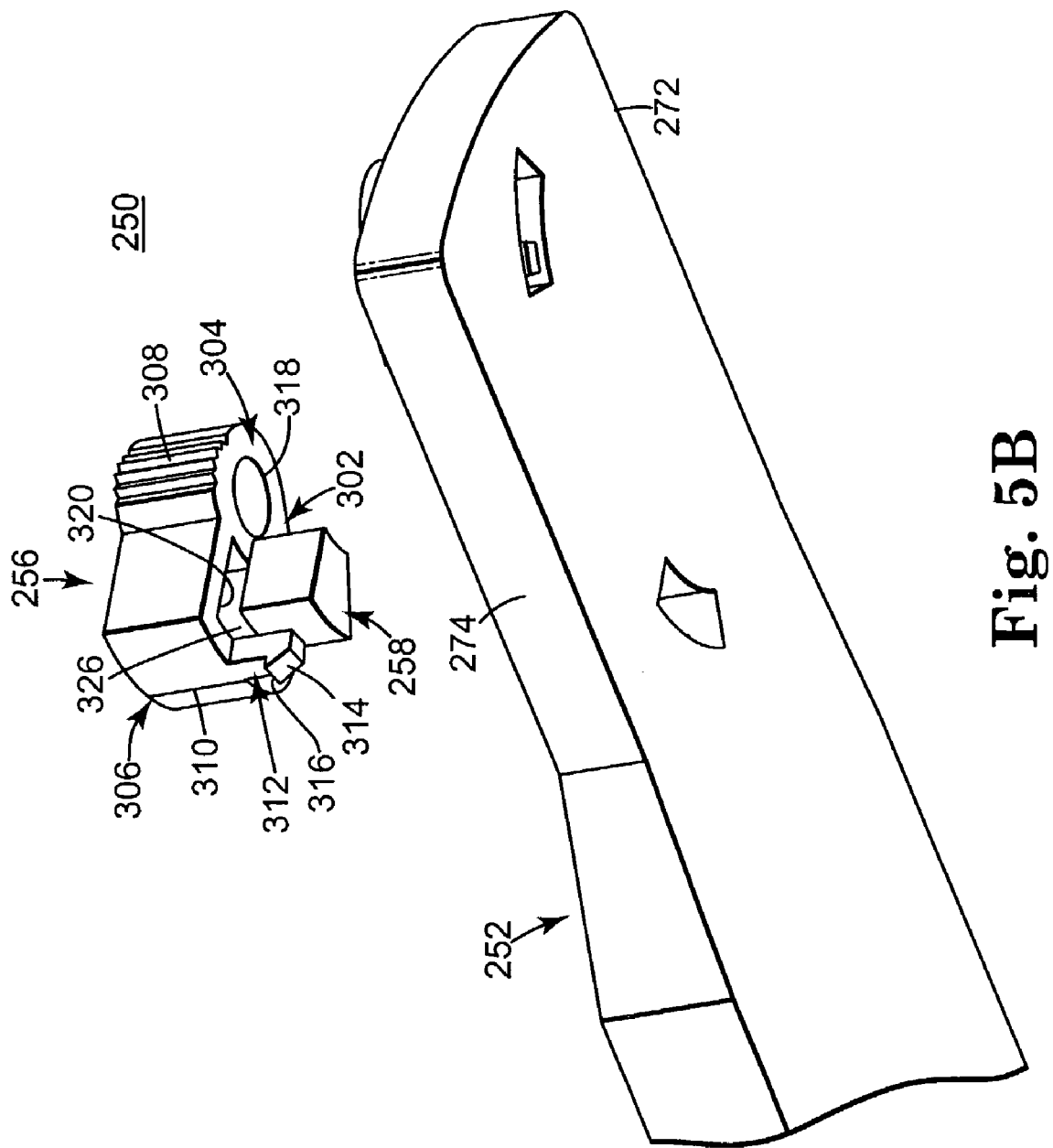

SURGICAL SUTURE HOLDING DEVICE

BACKGROUND OF THE INVENTION

The present invention relates to a device for holding a surgical suture. More particularly, it relates to a device for selectively retaining one or more surgical sutures useful in a variety of surgical applications, such as those requiring a surgical retractor.

A number of surgical procedures require the use of sutures. Beyond closing an incision or other tissue opening, sutures are commonly employed to assist in the delivery and/or securement of prosthetics, retaining tissue and/or moving tissue to a desired location, etc. With these and similar procedures, a relatively large number of sutures are required, each of which must be securely held at a desired position for select periods of time during the procedure.

One exemplary surgical procedure requiring use of multiple sutures is open-heart surgery. For example, a coronary artery bypass (CAB) procedure, such as a beating heart CAB procedure, entails the surgeon performing a sternotomy or a thoracotomy in order to gain access to the chest cavity. A retractor system is then employed to spread apart bones and other tissue, defining an opening for performing the surgical procedure. In this regard, a series of sutures are placed through relevant tissue, such as vessels on the surface of the heart. Other sutures are employed to pull back and retain sections of tissue so as to ensure complete access to the surgical site. These and other sutures must be securely and firmly held throughout the surgical procedure.

The sutures utilized with open chest surgeries, as well as numerous other surgical applications, can be retained in a variety of fashions. For example, the suture ends can be clamped to a surgical drape otherwise covering the patient. Alternatively, a number of suture holders/organizers have long been available for securing a series of sutures in an organized fashion. Exemplary surgical suture organizer/holders are described, for example, in U.S. Pat. No. 4,185,636 to Gabbay et al.; U.S. Pat. No. 4,492,229 to Grunwald; and U.S. Pat. No. 5,207,703 to Jain.

For most applications, the suture retaining structure must be configured to provide releasable attachment of the suture in a manner that readily permits re-positioning and re-locking of the suture relative to the holder device. That is to say, the surgeon will typically desire to pull (or further retract) the suture following engagement with the holder device. As such, a potentially viable suture holding design may incorporate a rope cleat-like device in which a rotatable cam, otherwise providing a toothed surface, is rotated into and out of engagement with a rope abutment structure, thereby gripping a rope therebetween. Exemplary cam-type rope cleats are described, for example, in U.S. Pat. No. 4,766,835 to Randall et al. and U.S. Pat. No. 4,899,423 to Randall. While useful for gripping a relatively thick rope, existing cam-type rope cleats are ill-suited for surgical applications. For example, the handling concerns associated with relatively delicate suture material is not present, and thus not addressed, by a rope cleat. Further, most surgical applications require that any tool or device employed therewith be highly compact; this requirement is not addressed by rope cleats. Instead, because space is not an issue, rope cleats are typically quite large.

U.S. Pat. No. 6,290,644 to Green, II et al. ("Green, II") represents one attempt at incorporating a cleat-like device into a surgical retractor system to provide suture holding capabilities. In particular, FIGS. 10 and 12 of Green, II illustrate locks 80 that are moveable within a channel 72 or 73. The locks 80 are not true cam cleats, as they are externally captured within a recess 74 or 75 and require an external bearing wall to effectuate a cam-like motion. During use, the channels 71 and 72 or 73 are necessary to facilitate a desired suture location. Unfortunately, the channels 71, 72, 73 to can overtly impede a surgeon's ability to readily visually confirm suture engagement and limit suture positioning in front of and behind the locks 80. Also, resilient foam pieces 85 must be adhered to the respective locks 80 as the locks 80 themselves are not capable of independently maintaining the pieces 85. As a result, the foam pieces 85 can easily separate from the corresponding lock 80, potentially leading to poor suture holding capabilities.

Many surgical procedures require selective holding of one or more sutures. While suture holding devices have long been available, certain drawbacks remain. Therefore, a need exists for a surgical suture holding device adapted to facilitate rapid assembly and disassembly of a suture thereto, along with providing the surgeon with the ability to visually confirm proper suture positioning relative to the holding device.

SUMMARY OF THE INVENTION

One aspect of the present invention relates to a device for holding a surgical suture. The device includes a base, a guide body, a cam body, a bearing member, and a spring member. The base has a top side, a front edge, and a back edge. The guide body projects from the top side of the base and defines a guide face. In this regard, the guide face has an entrance side and an exit side, with the guide body being positioned such that the entrance side is adjacent the front edge of the base and the exit side is adjacent the back edge of the base. The cam body is pivotally mounted to the top side of the base and forms a toothed surface positioned to selectively secure a surgical suture against the guide face. In particular, the cam body is positioned such that the surgical suture is secured between the toothed surface and the guide face when the suture is tensioned in the first direction and releases the suture when the suture is tensioned in an opposite direction. The spring member is positioned between the cam body and the bearing member such that the spring member biases the toothed surface toward the guide face. In addition to the above components, the device of one embodiment is characterized by an absence of a channel formed at the front edge of the base opposite the entrance side of the guide body. With this first embodiment construction, a suture can easily be positioned between the toothed surface and the guide face, and engagement therebetween easily visually confirmed. In one preferred embodiment, the holding device is adapted to be a surgical retractor insert, and forms a handle at a trailing end thereof that facilitates insertion/removal of the holding device relative to the surgical frame.

Another aspect of the present invention relates to a device for holding a surgical suture, and includes a base, a guide body, a cam body, a bearing member and a spring member. The guide body projects from a top side of the base, and defines a guide face having an entrance side and an exit side. The cam body is pivotally mounted to the top side of the base and forms a toothed surface. In addition, the cam body is adapted to maintain a spring member. Upon final assembly, the maintained spring member contacts the bearing member such that the spring member biases the toothed surface toward the guide face. In this regard, the toothed surface is positioned to secure a surgical suture between the toothed surface and the guide face when the suture is tensioned in a first direction, and release the surgical suture when the suture is tensioned in a second direction. In one preferred embodiment, the spring member is an arm integrally formed with the cam body. In another preferred embodiment, the spring member is retained within an internal bore formed by the cam body.

Yet another aspect of the present invention relates to a device for holding a surgical suture. The device includes a base, a guide body, a cam body, a bearing member, and a spring member. The base has a top side, a front edge, and a back edge. The top side defines an uppermost, elongated planar surface of the base. The guide body projects from the top side of the base and defines a guide face. In this regard, the guide face has an entrance side and an exit side, with the guide body being positioned such that the entrance side is adjacent the front edge of the base and the exit side is adjacent the back edge of the base. The cam body is pivotally mounted to the top side of the base and forms a toothed surface positioned to selectively secure a surgical suture against the guide face. In particular, the cam body is positioned such that the surgical suture is secured between the toothed surface and the guide face when the suture is tensioned in the first direction and releases the suture when the suture is tensioned in an opposite direction. The spring member is positioned between the cam body and the bearing member such that the spring member biases the toothed surface toward the guide face.

Yet another aspect of the present invention relates to a method of holding a surgical suture, the method includes providing a suture holding device that includes a base, a guide body, a cam body, a bearing member, and a spring body. The guide body projects from a top side of the base and defines a guide face having an entrance side and an exit side. The cam body is pivotally mounted to the top side of the base and forms a toothed surface. The spring member is disposed between the cam body and the bearing member, and biases the toothed surface toward the guide face. Finally, an engagement region is defined relative to a length of the guide face, with the holding device being characterized by an absence of a rigidly defined channel in the engagement region. A surgical suture is also provided that defines a leading section and intermediate section, and a trailing section. The intermediate section is positioned at the engagement region between the toothed surface and the guide face. In particular, the surgical suture is positioned such that the leading section extends from the entrance side of the guide face and the trailing section extends from the exit side of the guide face. Finally, the leading section is tensioned away from the entrance side of the guide face such that the toothed surface frictionally locks the intermediate section against the guide face.

BRIEF DESCRIPTION OF THE DRAWINGS

FIG. 4B is a bottom perspective view of a holding device useful with the system of FIG. 4A;

FIG. 5B is a bottom, exploded view of the suture holding device of FIG. 5A;

DETAILED DESCRIPTION OF THE PREFERRED EMBODIMENTS

Figure 1:
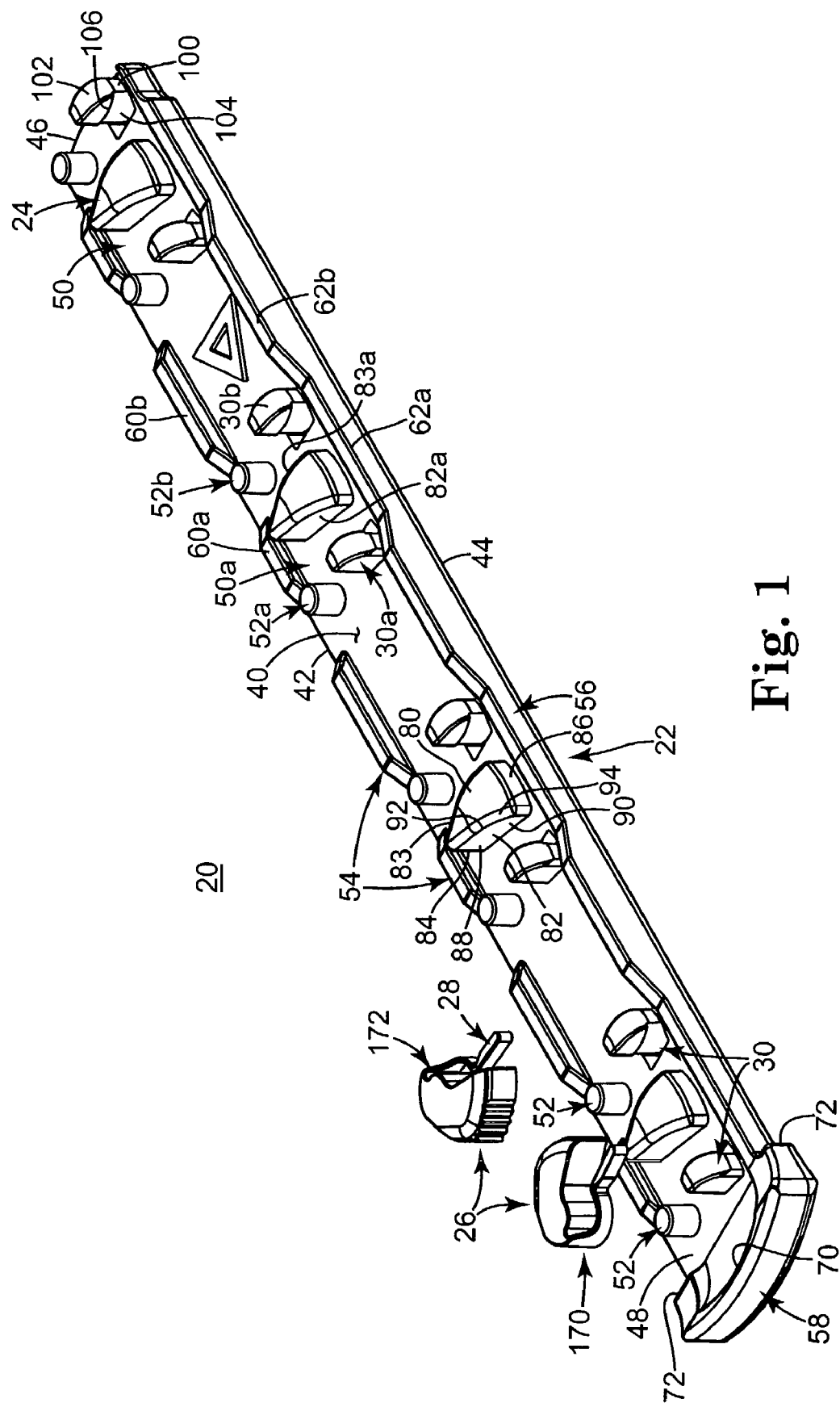
FIG. 1 is a perspective, partially exploded view of a suture holding device in accordance with one embodiment of the present invention.

One embodiment of a suture holding device 20 in accordance with the present invention is shown in FIG. 1. The holding device 20 includes a base 22, at least one guide body 24, at least one cam body 26, at least one spring member 28, and at least one bearing member 30. Details on the various components are provided below. In general terms, however, the device 20 preferably includes a plurality of the guide bodies 24 extending from the base 22. Similarly, a plurality of cam bodies 26 (two of which are shown in FIG. 1) are provided, each being pivotally mounted to the base 22 adjacent opposite sides of one of the guide bodies 24. One of the spring members 28 is connected to a corresponding one of the cam bodies 26 and, upon final assembly, contacts a portion of one of the bearing members 30. The spring member 28 biases a portion of the cam body 26 toward the corresponding guide body 24, facilitating securement of a surgical suture (not shown) between the cam body 26 and the guide body 24.

The base 22 is, in one embodiment, an elongated body defining a top side 40, a bottom side (hidden in FIG. 1), a front edge 42, a back edge 44, a leading end 46, and a trailing end 48. The top side 40 defines an uppermost, elongated planar surface of the base 22 along which various other components of the holding device 20 are provided. With this in mind, and in one preferred embodiment, a plurality of suture securement zones 50 (referenced generally in FIG. 1) are definable along a length of the top side 40. Each of the securement zones 50 includes one of the guide bodies 24, an opposing pair of the cam bodies 26 (each having an associated one of the spring members 28), and an opposing pair of the bearing members 30.

In addition to the guide bodies 24, the cam bodies 26 and the bearing members 30, various other components of the holding device 20 project from and/or are mounted to the top side 40 of the base 22. For example, in one embodiment an opposing pair of pins 52 are provided within each of the securement zones 50, a first shoulder 54 is formed along the front edge 42, a second shoulder 56 is formed along the back edge 44, and a handle 58 is formed at the trailing end 48. Each of the pins 52 are sized to pivotally maintain a respective one of the cam bodies 26, and are preferably in the form of a cylindrical body. Alternatively, other constructions are acceptable. For example, one or more of the pins 52 can define half circles in transverse cross-section. Regardless, in one embodiment, the pins 52 are bosses integrally formed with the base 22.

The first shoulder 54 preferably includes a plurality of intermittent shoulder segments 60 (referenced generally in FIG. 1), including shoulder segments 60a and 60b. The shoulder segments 60 are, in one embodiment, intermittently positioned along the front edge 42, with each securement zone 50 including the segment 60a, and the segment 60b positioned between adjacent ones of the securement zones 50. In one embodiment, the segments 60a, 60b have differing heights (or extensions relative to the top side 40), although a uniform height can be employed. Further, the first shoulder 54 can be continuous. Alternatively, the first shoulder 54 can be omitted.

Similarly, the second shoulder 56 extends from the top side 40 along the back edge 44. In one embodiment, the second shoulder 56 includes shoulder segments 62 (referenced generally in FIG. 1), including segment 62a and 62b. Respective ones of the segments 62a are provided in each of the securement zones 50, whereas respective ones of the segments 60b are provided between adjacent ones of the securement zones 50. With the embodiment of FIG. 1, the segments 62b have a height greater than that of the segment 62a, although a more uniform height can be provided. Alternatively, the second shoulder 56 can be omitted. Where provided, however, the first and second shoulders 54, 56 facilitate insertion of the holding device 20 within a surgical frame (not shown) as described in greater detail below. To this end, a maximum height of the second shoulder 56 is greater than a maximum height of the first shoulder 54 so as to ensure proper orientation of the holding device 20 relative to the surgical frame.

The handle 58 is formed at the trailing end 48 of the base 22, and includes a grip portion 70 extending upwardly relative to the top side 40. The grip portion 70 provides a convenient surface for placement of a user's finger(s) (not shown) for handling of the holding device 20. For example, the grip portion 70 preferably forms a curved region that is easily grasped by the user. As described in greater detail below, a bottom surface (not shown in FIG. 1) of the handle 58 further forms an additional grasping surface. Finally, in one embodiment, the handle 58 defines a width that is greater than a width of the remainder of the base 22, defining opposing stop surfaces 72. With this one preferred construction, and as described in greater detail below, the stop surfaces 72 dictate a desired insertion position of the holding device 20 relative to a surgical frame (not shown). Alternatively, other constructions for the handle 58 are acceptable, or the handle 58 can be eliminated.

The guide bodies 24 are, in one embodiment, formed as projections from the top side 40. Alternatively, the guide bodies 24 can be separately formed and assembled to the top side 40. Regardless, the guide bodies 24 are preferably wedge-shaped, defining a top surface 80, opposing guide faces 82, 83 (one guide face 82 is shown for each of the guide bodies 24 in FIG. 1 with the opposing guide face 83 being hidden in the view but referenced generally), an apex 84 and a back wall 86. The guide faces 82, 83 extend between the apex 84 and the back wall 86, and each define an entrance side 88 and an exit side 90. With these conventions in mind, the guide bodies 24 are positioned such that the apex 84, and thus the entrance side 88, is adjacent the front edge 42 of the base 22, whereas the back wall 86, and thus the exit side 90, is adjacent the back edge 44.

The guide faces 82, 83 are preferably identical, flat surfaces, extending perpendicular relative to a plane of the top side 40. Further, the guide faces 82, 83 preferably taper in height from the entrance side 88 to the exit side 90. More particularly, a top edge 92 of each of the guide faces 82, 83 preferably curves downwardly, toward the top side 40, from the entrance side 88 to the exit side 90. This preferred low-profile configuration is mimicked by the top surface 80 that similarly curves from the apex 84 to the back wall 86. With this one preferred construction, then, a height of the apex 84 is greater than a height of the back wall 86 (relative to the top side 40). Sharp corners along the top surface 80 are eliminated, thereby minimizing the opportunity for undesirable suture damage. Similarly, a transition region 94 is preferably formed between the top edge 92 of the guide faces 82, 83 and the top surface 80. In one embodiment, the transition region 94 is curved in transverse cross-section, further eliminating any potentially sharp corners that might otherwise damage a suture contacting the guide body 24.

The bearing members 30 are preferably formed as projections from the top side 40, although the bearing members 30 can alternatively be separately formed and assembled to the top side 40. Regardless, and with one embodiment, one bearing member 30 is provided at opposite sides of the guide body 24 within each of the respective securement zones 50. Further, each of the bearing members 30 includes a lower segment 100 and a head 102. The lower segment 100 extends from the top side 40 and defines a contact surface 104. The head 102 extends from the lower segment 100 opposite the top side 40, forming an inwardly projecting ledge 106 (relative to the corresponding guide body 24). As described in greater detail below, the contact surface 104 is configured to engage a portion of a corresponding spring member 28, such that the spring member 28 bears against the contact surface 104. The ledge 106 is configured to lock the spring member 28 relative to the bearing member 30.

In one embodiment, other than the ledge 106, exposed surfaces of the bearing member 30 are smoothed so as to avoid deleterious contact with a suture (not shown). Thus, for example, a top surface 108 of the head 102 is preferably curved. Alternatively, other constructions for the bearing member 30 are acceptable.

Figure 2A:
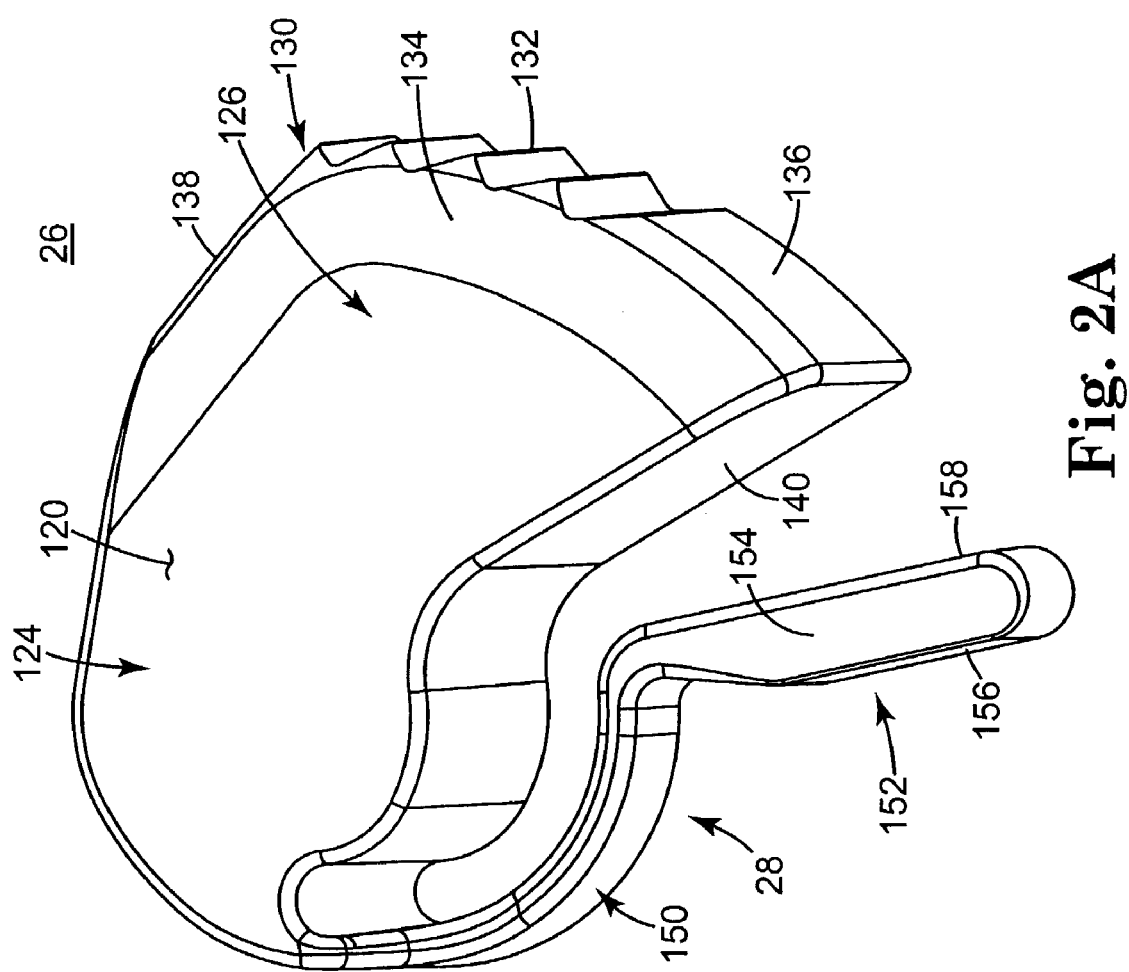
FIG. 2A is an enlarged, top perspective view of a cam portion of the device of FIG. 1.
Figure 2B:
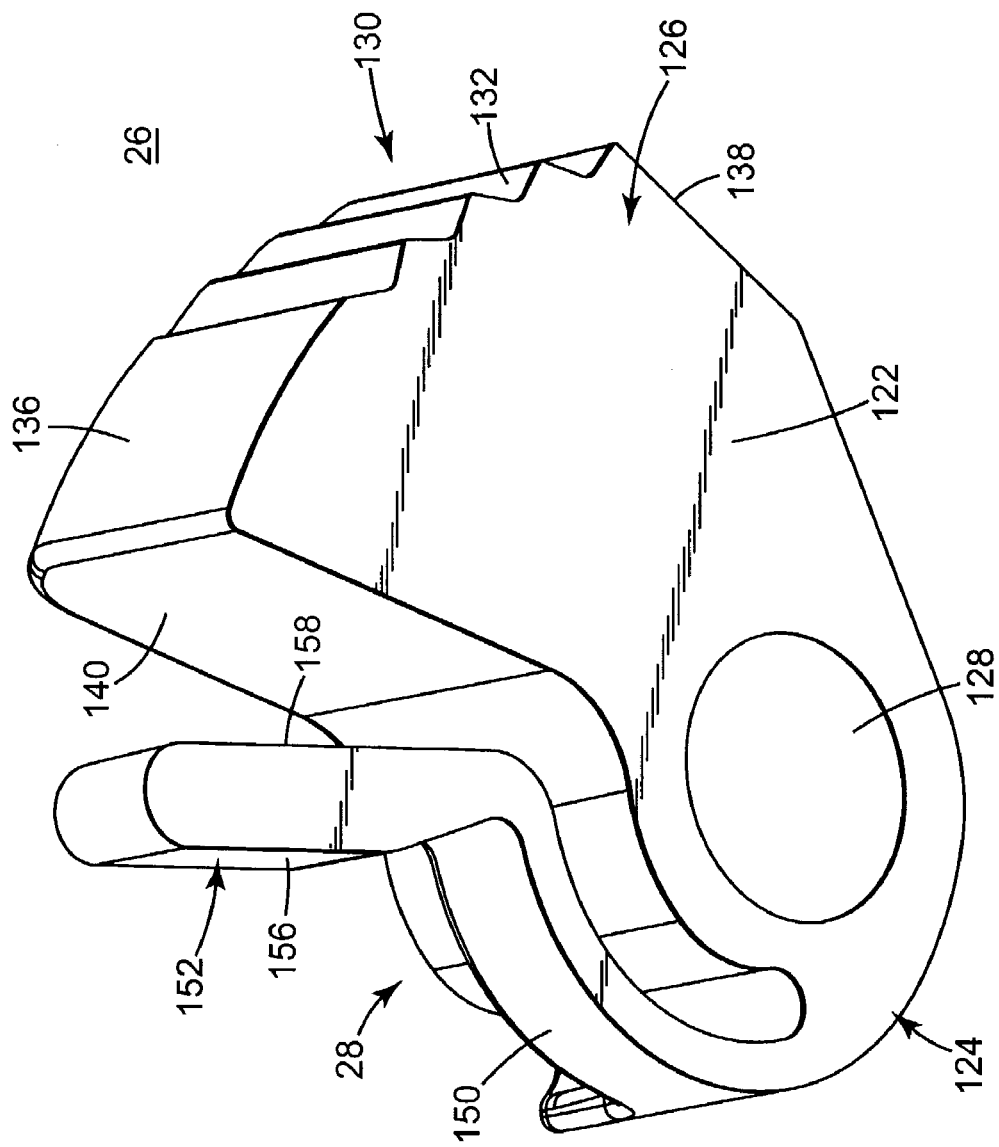
FIG. 2B is an enlarged, bottom perspective view of the cam of FIG. 2A.

One embodiment of the cam body 26 and the spring member 28 are shown in greater detail in FIGS. 2A and 2B, it being understood that each of the cam bodies 26 shown in FIG. 1 are essentially identical. With this one embodiment, the cam body 26 and the spring member 28 are integrally formed as a unitary body. With this in mind, the cam body 26 defines an upper side 120 (best shown in FIG. 2A), a lower side 122 (best shown in FIG. 2B), a fixed end 124, and a free end 126. An internal bore 128 (best shown in FIG. 2B) is formed at the fixed end 124, extending from the lower side 122. Finally, the free end 126 extends from the fixed end 124, terminating in a leading side 130 forming a toothed surface 132. In general terms, and with additional reference to FIG. 1, upon final assembly, the cam body 26 is mounted to the base 22 with the internal bore 128 receiving a respective one of the pins 52. In this regard, the fixed end 124 is pivotally mounted relative to the top side 40 of the base 22 via the pin 52, and the toothed surface 132 faces one of the guide faces 82 or 83 of a respective one of the guide bodies 24.

The upper side 120 extends from the fixed end 124 to the free end 126, and is preferably smooth. In one embodiment, the upper side 120 defines a transition region 134 at the free end 126 adjacent the leading side 130. The transition region 134 is preferably curved in transverse cross-section, minimizing the formation of one or more sharp corners between the upper side 120 and the leading side 130. Alternatively, other configurations are acceptable.

The leading side 130 includes a clearance surface 136 that, in combination with the toothed surface 132, defines a continuous radius of curvature. The clearance surface 136 is preferably smooth and, as described in greater detail below, facilitates suture orientation at a wide number of angular positions relative to the toothed surface 132. Alternatively, the clearance surface 136 can be eliminated or adapted to provide teeth. Additionally, the leading side 130 includes an entry portion 138 extending from the toothed surface 132 opposite the clearance surface 136. Extension of the entry portion 138 relative to a radius of curvature defined by the toothed surface 132 and the clearance surface 136 is adapted to not overtly limit an angular orientation of a surgical suture (not shown) relative to the toothed surface 132. That is to say, the entry portion 138 is not continuous with the radius of curvature of the toothed surface 132/clearance surface 136; instead, the extension of the entry portion 138 defines an angle in the range of 90°-120° relative to an end of the toothed surface 132. With this one preferred construction, the entry portion 138 does not form a sharp, 90° corner (that might otherwise damage a suture), yet provides sufficient room for desired extension of the suture from the toothed surface 132.

Finally, the cam body 26 preferably forms a receiving surface 140 as an extension from the clearance surface 136 opposite the toothed surface 132. The receiving surface 140 is preferably flat, having dimensions and an angular orientation adapted to correspond with a portion of the spring member 28 as described below.

With the embodiment of FIGS. 2A and 2B, the spring member 28 is an arm extending from the fixed end 124 of the cam body 26. More particularly, the spring member 28 includes a torsion section 150 and a leading section 152. The torsion section 150 is connected to the fixed end 124 of the cam body 26. The leading section 152 extends from the torsion section 150 opposite the cam body 26.

In one embodiment, the torsion section 150 and the leading section 152 define a relatively uniform height that is less than a height of the cam body 26. Alternatively, the torsion section 150 and the leading section 152 can have differing heights and/or can define a height commensurate with that of the cam body 26. Regardless, the torsion section 150 defines a curve, with a material selection and thickness of the torsion section 150 being such that the curve biases the leading section 152 away from the receiving surface 140 of the cam body 26. That is to say, the torsion section 150 establishes a relaxed state spacing between the leading section 152 and the receiving surface 140. However, a spring force established by the torsion section 150 can be overcome such that in a contracted state, a spacing between the leading section 152 and the receiving surface 140 is decreased relative to the relaxed state spacing. In one embodiment, the leading section 152 contacts the receiving surface 140 in the compressed state, as described below.

The leading section 152 extends in a generally linear fashion from the torsion section 150 as shown, and defines an upper surface 154, a contact surface 156, and a stop surface 158. The contact surface 156 and the stop surface 158 are preferably parallel to one another, with the contact surface 156 providing a relatively large surface area for engaging a corresponding surface of the bearing member 30 (FIG. 1) as described below. Conversely, the stop surface 158 preferably defines an angular extension relative to the torsion section 150 such that in a fully compressed state, the stop surface 158 is flush against the receiving surface 140 of the cam body 26.

As previously described, the cam body 26 and the spring member 28 are, in one embodiment, integrally formed as a unitary body. In this regard, the combination cam body 26/spring member 28 is formed of a hardened, surgical safe material, such as plastic, stainless steel, or other metals, etc. More particularly, and in one preferred embodiment, the combination cam body 26/spring member 28 is a molded polymer such as polyetherimide (available under the trade name Ultem®). Alternatively other materials and manufacturing techniques can be employed. Regardless, the spring member 28 is preferably constructed to provide a spring force in the range of 0.01-0.50 lbs, more preferably 0.1-0.25 lbs.

Figure 3:
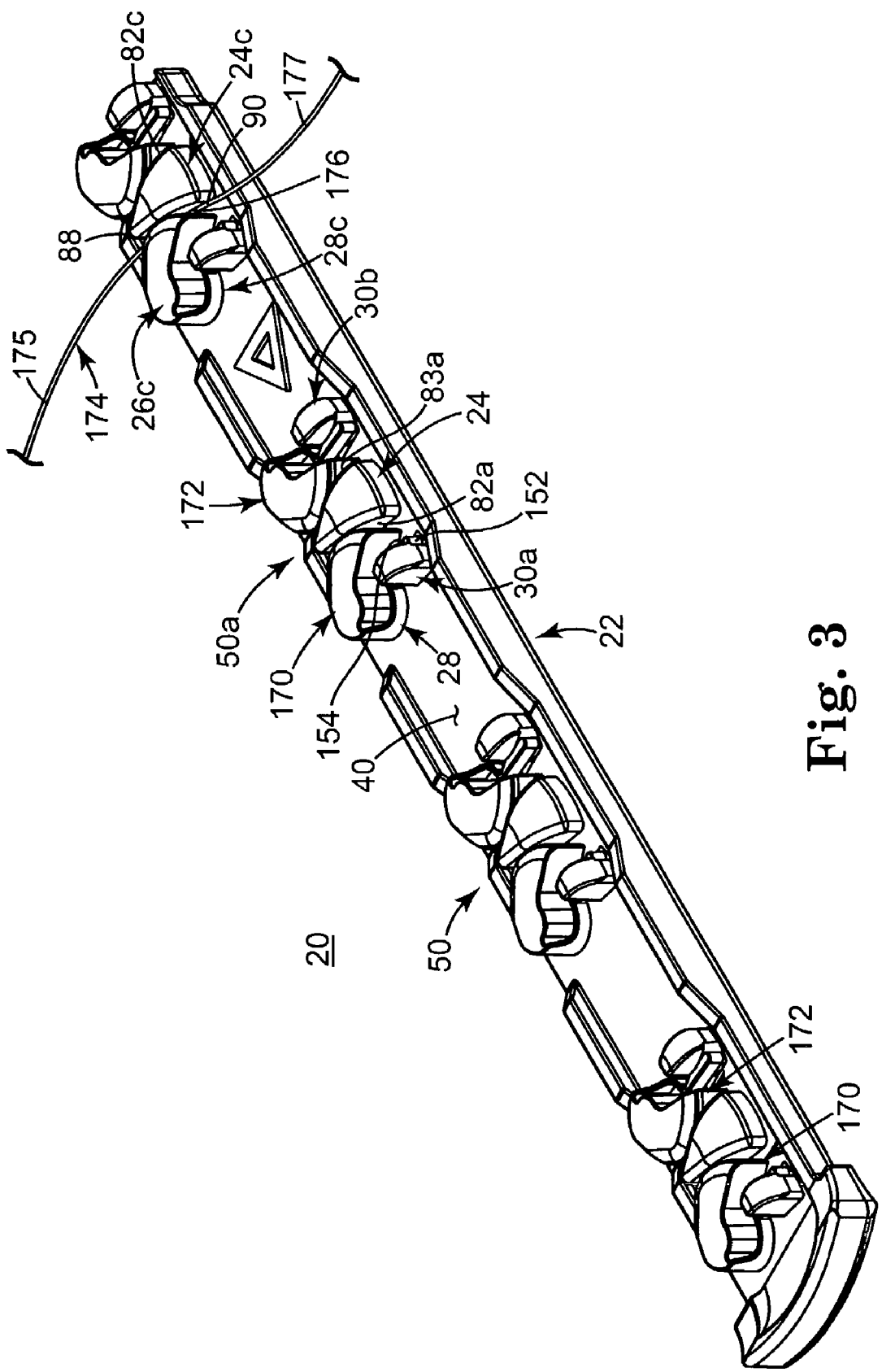
FIG. 3 is a top, perspective view of the device of FIG. 1 upon final assembly.

With reference to FIGS. 1-3, the cam bodies 26 are assembled to the base 22 as follows. As previously described, each of the combination cam body 26/spring member 28 illustrated in FIGS. 1 and 3 are virtually identical. Relative to each of the securement zones 50, however, the corresponding pair of cam bodies 26/spring members 28 have a reverse configuration. More particularly, and with reference to the orientation of FIGS. 1 and 3, each of the securement zones 50 is, in one embodiment, provided with a left cam body/spring member 170 and a right cam body/spring member 172. The left cam body/spring member 170 and the right cam body/ spring member 172 mirror one another, but are otherwise identical. As a point of reference, FIGS. 2A and 2B illustrate a left cam body/spring member configuration.

With these designations in mind, then, the left cam body/ spring member 170 is assembled adjacent a corresponding one of the guide faces 82 of a corresponding one of the guide bodies 24. For example, relative to the securement zone 50a, the left cam body/spring member 170 is mounted over the pin 52a (shown in FIG. 1). In particular, the pin 52a is received within the internal bore 128 (FIG. 2B), and oriented such that the toothed surface 132 faces the corresponding guide body 24, and in particular a corresponding guide face (designated as 82a in FIGS. 1 and 3). The leading section 152 of the left cam body/spring member 170 is secured to a corresponding one of the bearing members 30 (designated as 30a in FIGS. 1 and 3). In particular, the upper surface 154 is captured beneath the ledge 106 (best shown in FIG. 1) provided by the bearing member 30a. In this regard, a spacing between the guide face 82a and the bearing member 30a is such that the toothed surface 132 (hidden in FIG. 3) contacts the guide face 82a, whereas the contact surface 156 (best shown in FIG. 2A) of the spring member 28 abuts the contact surface 104 (best shown in FIG. 1) of the bearing member 30a, with the spring member 28 being slightly compressed from the relaxed state. This slight compression dictates that the upper surface 154 consistently nests beneath the ledge 106 of the bearing member 30a. The right cam body/spring member 172 is similarly assembled to the pin 52b (FIG. 1) and the bearing member 30b, with the toothed surface 132 (hidden in FIG. 3) of the right cam body/spring member 172 contacting the opposing guide face (hidden in FIGS. 1 and 3, but referenced generally at 83a). Similarly, pairs of the cam body/spring members 170, 172 are mounted within respective ones of the remaining securement zones 50.

During use, and with specific reference to FIG. 3, a surgical suture 174 is selectively secured between the cam body 26 and one of the guide faces 82 or 83. For example, the suture 174 can be defined as including a leading segment 175, an intermediate segment 176, and a trailing segment 177. The suture 174 can be secured between one of the cam bodies (referenced at 26c in FIG. 3) and the corresponding guide body 24c by positioning the intermediate segment 176 above the interface between the toothed surface 132 (hidden in FIG. 3, but shown in FIG. 2A) of the cam body 26c and the guide face 82c of the guide body 24c. By applying downward pressure on the intermediate segment 176 and pulling slightly on the trailing segment 177 relative to the exit side 90 of the guide face 82c, the intermediate segment 176 will slide between the toothed surface 132 and the guide face 82c. Once the downward pressure is released, friction between the intermediate segment 176 and the toothed surface 132 (hidden in FIG. 3 for the cam body 26c), as well as the tension generated by the spring member 28c, causes the cam body 26c to press the intermediate segment 176 against the guide face 82c, thus securing the surgical suture 174 relative to the suture holding device 20. Depending upon a construction of the cam body 26c, the intermediate segment 176 can be against the guide face 182c at any point along a length thereof, such that the guide face 182c effectively defines an engagement region. The leading segment 175 extends from the entrance side 88 of the guide face 82c, whereas the trailing segment 177 extends from the exit side 90. In accordance with one embodiment of the suture holding device 20, the leading segment 175 can be maneuvered to a wide variety of angular orientations relative to the guide body 24c and the cam body 26c. Similarly, the trailing segment 177 can be maneuvered to a large number of angular orientations relative to the secured intermediate segment 176.

The surgical suture 174 can be released from the suture holding device 20 by tensioning the trailing segment 177 away from the exit side 90 of the guide face 82c while at the same time lifting the intermediate segment 176 away from the guide body 24c/cam body 26c. When sufficient tension is applied to overcome a bias of the spring member 28c, the cam body 26c will pivot about the corresponding pin (not shown), such that the toothed surface 132 moves away from the guide face 82c, thus releasing the surgical suture 174.

The relatively open construction of the suture holding device 20 allows a user (e.g., surgeon) to readily view all components as well as visually confirm desired engagement of the suture 174. Other than a corresponding one of the cam bodies 26, no material and/or structure is positioned opposite the guide faces 82, 83 so that the suture 174 is easily seen. The top side 40 is preferably free of material between adjacent securement zones 50, thus affording a user the ability to easily remove and replace problematic components (e.g., a worn cam body 26).

Figure 4A:
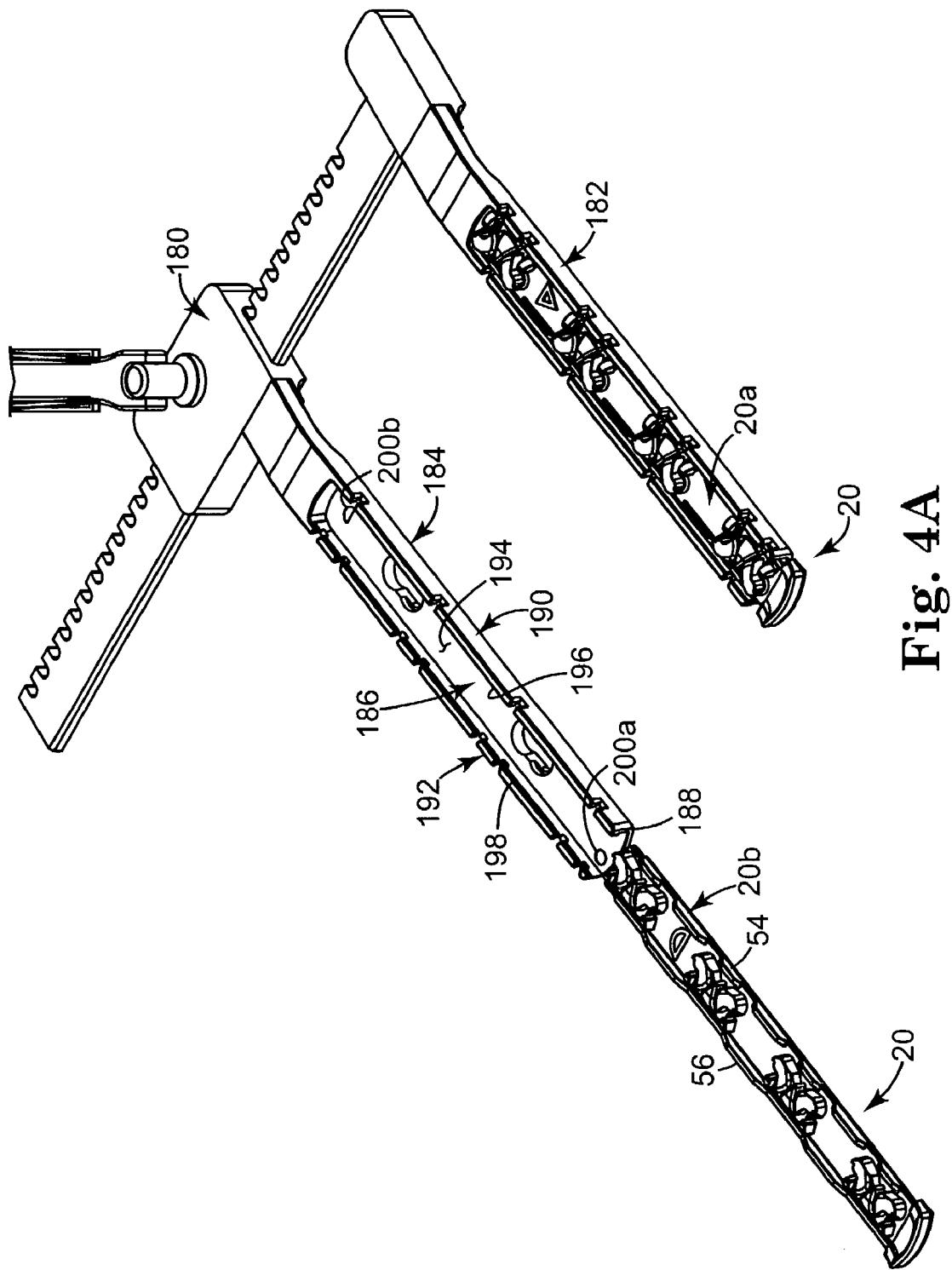
FIG. 4A is a perspective view of two of the holding devices of FIG. 1 partially assembled to a surgical retractor system.

During use, the suture holding device 20 can be maintained relative to a surgical site in a variety of fashions. For example, the suture holding device 20 can be attached to a surgical drape otherwise placed over the patient, such as by clips (not shown). Alternatively, the suture holding device 20 can be attached or assembled to a separate medical device that is convenient to the surgical operation. For example, FIG. 4A depicts a surgical retractor system 180 commonly employed with various surgical applications, such as those requiring a median sternotomy. One such surgical retractor system is available under the trade name "OctoBase" from Medtronic, Inc., of Minneapolis, Minn. Regardless, the surgical retractor system 180 includes a pair of opposing, first and second frame segments 182, 184 each identically forming a recess 186 having an open end 188. The recess 186 is defined in part by a first wall 190, a second wall 192, and a bottom 194. Each of the walls 190, 192 forms an inwardly projecting ridge 196, 198, respectively. In this regard, a spacing between the bottom 194 and the ridge 196 of the first wall 190 is different from a spacing between the bottom 194 and the ridge 198 of the second wall 192. Finally, the bottom 194 defines first and second apertures 200a, 200b. The aperture 200a is positioned adjacent the open end 188, whereas the second aperture 200b is formed adjacent an opposite end of the slot 186.

In one embodiment, the suture holding device 20 is a replaceable insert useful with the surgical retractor system 180 of FIG. 4A. In this regard, FIG. 4A illustrates one of the suture holding devices (referenced as 20a in FIG. 4A) assembled to the first frame segment 182, whereas a second one of the suture holding devices (referenced as 20b in FIG. 4A) is positioned relative to the second frame segment 184 prior to insertion (or following disassembly from the second frame segment 184). The suture holding device 20a or 20b is assembled to the corresponding frame segment 182 or 184 by sliding the base 22 within the recess 186. In this regard, the suture holding device 20a or 20b is constructed so as to facilitate proper orientation relative to the corresponding frame segment 182 or 184. Though identical in general design, the frame segments 182, 184 are provided and oriented as mirror images. To satisfy this construction, then, the suture holding device 20 is preferably formed as either a right holding device 20a or a left holding device 20b (relative to the orientation of FIG. 4A). The right holding device 20a corresponds with the first frame segment 182, whereas the left holding device 20b corresponds with the second frame segment 184. To ensure that the right holding device 20a is not inadvertently inserted within the second frame segment 184 and/or that the left holding device 20b is not inadvertently inserted within the first frame segment 182, a height of the first and second shoulders 54, 56 provided with the suture holding device 20a or 20b varies as previously described. More particularly, a height of the first shoulder 54 corresponds with a spacing between the ridge 196 of the first wall 190 and the bottom 194, whereas a height of the second shoulder 56 corresponds with a spacing between the ridge 198 of the second wall 192 and the bottom 194. Thus, when inserting the right suture holding device 20a into the first frame segment 182, the first shoulder 54 can be received between the ridge 196 and the bottom wall 194, and the second shoulder 56 can be received between the ridge 198 and the bottom 194. However, if an attempt were made to insert the right suture holding device 20a into the second frame segment 184, the second shoulder 56 would not "fit" beneath the ridge 196 of the first wall 190, such that the right suture holding device 20a could not be inserted.

Once properly inserted, the handle 58 preferably provided with the suture holding device 20a or 20b provides a convenient surface for quickly removing the suture holding device 20a or 20b from the corresponding frame segment 182 or 184 when so desired. Finally, and in one preferred embodiment, a pair of projections 202a, 202b are formed along a bottom side 204 of the base 22 as shown in FIG. 4B. The projections 202a, 202b correspond with the apertures 200a, 200b (FIG. 4A) formed in the frame segment slot 186. When properly assembled, the projections 202a, 202b nest within the corresponding apertures 200a, 200b, promoting engagement between the suture holding device 20a or 20b and the corresponding frame segment 182 or 184.

While the suture holding device 20 has been described as preferably including a plurality of the guide bodies 24, each having an opposing pair of the combination cam body 26/spring member 28 mounted adjacent thereto, other configurations are acceptable. For example, the guide body 24 can be configured so as to interact with only a single cam body. Further, the suture holding device 20 need not include a plurality of the guide bodies 24; in fact, only a single one of the guide bodies 24 and a single one of the cam bodies 26 need be provided. In addition, alternative configurations of the cam body 26 and/or the spring member 28 may also be employed.

Figure 5A:
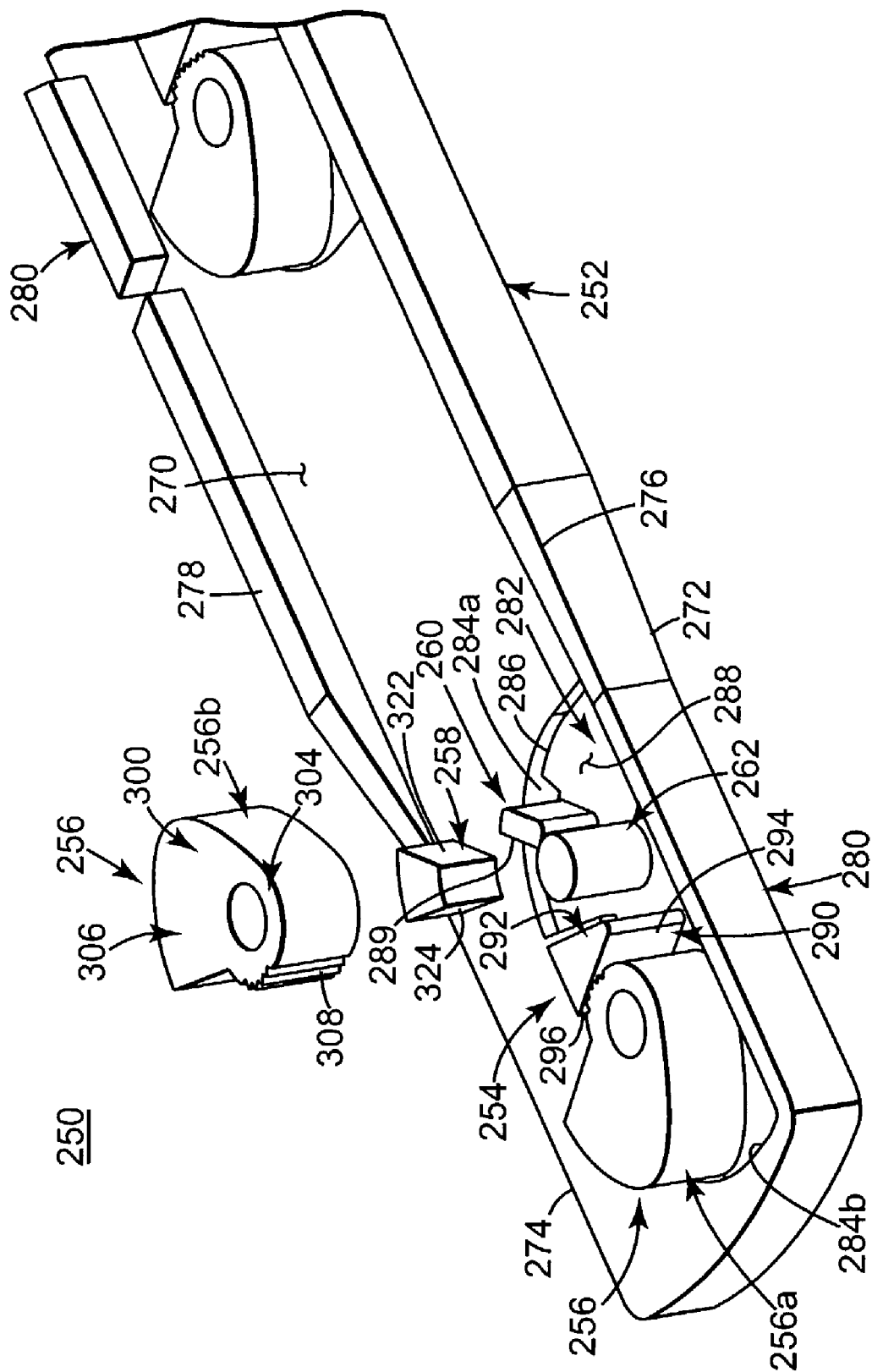
FIG. 5A is a top, exploded view of a portion of an alternative embodiment suture holding device.

For example, a portion of an alternative embodiment suture holding device 250 is shown in FIGS. 5A and 5B. The holding device 250 includes a base 252, at least one guide body 254 (referenced generally in FIGS. 5A and 5B), and at least one cam body 256 (referenced generally in FIGS. 5A and 5B). Further, a spring member 258 is provided with each cam body 256, as is a bearing member 260 and a pin 262. The various components are described in greater detail below. In general terms, however, the spring member 258 is retained within the cam body 256 that in turn is assembled over the bearing member 260 and the pin 262. The pin 262 serves as a pivot point for movement of the cam body 256 relative to the guide body 254, with the spring member 258 biasing (via interaction with the bearing member 260) a relevant portion of the cam body 256 toward the guide body 254.

The base 252 is similar to the base 22 (FIG. 1) previously described, and defines a planar top side 270, a front edge 272, and a back edge 274. In one embodiment, the base 252 includes further features previously described with respect to the base 22 (FIG. 1), such as first and second shoulders 276, 278 extending from the top side 270 along the front and back edges 272, 274, respectively, as well as a handle (not shown) and a trailing end thereof.

The one or more guide bodies 254, bearing member(s) 260, and pin(s) 262 are preferably formed as extensions or projections from the top side 270. In this regard, a location of each guide body 254 defines a suture securement zone (referenced generally at 280 in FIG. 5A). More particularly, and with the one embodiment of FIGS. 5A and 5B, each securement zone 280 includes one of the guide bodies 254, and opposing pairs of the cam bodies 256, spring members 258, bearing members 260, and pins 262. With these designations in mind, and in one embodiment, a receiving region 282 is defined in the top side 270 within each of the securement zones 280. The receiving region 282 is a partial recess relative to the top side 270, extending along opposite sides of each of the guide body 254. In this regard, the receiving region 282 is adapted to receive two of, the cam bodies 254 as shown in FIG. 5A. With this one embodiment, the guide body 254, bearing members 260, and pins 262 associated with the securement zone 280 are formed or provided within the receiving region 282. A portion of the receiving region 282 is defined by peripheral walls 284a, 284b extending in an arcuate fashion at opposite sides of the guide body 254. The peripheral walls 284a, 284b each form a ridge 286 that is raised relative to a bottom wall 288 of the receiving region 282.

The bearing member 260 is positioned within the receiving region 282, with opposing ones of the bearing members 260 preferably being provided adjacent opposite sides of a corresponding one of the guide bodies 254 (it being understood that FIG. 5A illustrates one of the bearing members 260; the opposing bearing member 260 is covered by a corresponding cam body 256). The bearing member 260 is preferably generally rectangular in transverse cross-section, although other shapes are acceptable. Regardless, the bearing member 260 defines a bearing surface 289.

The pin 262 is similarly positioned within the receiving region 282, with opposing ones of the pins 262 preferably being provided adjacent opposite sides of the corresponding guide body 254 (it being noted that FIG. 5A illustrates one of the pins 262; the opposing pins 260 is covered by a corresponding cam body 25b). As with previous embodiments, the pin 260 is preferably a cylindrical boss, although other shapes/configurations are acceptable.

In one embodiment, the guide body 254 is a wedge-shaped member defining opposing guide faces 290, 292 (the guide face 292 being referenced generally in FIG. 5A). Each of the guide faces 290, 292 defines an entrance side 294 and an exit side 296. The guide body 254 is positioned relative to the base 252 such that the entrance side 294 is adjacent the front edge 272 and the exit side 296 is adjacent the back edge 274.

The cam body 256 defines an upper side 300 (best shown in FIG. 5A), a lower side 302 (best shown in FIG. 5B), a fixed end 304, and a free end 306. A toothed surface 308 is formed adjacent the fixed end 304. Further, and as best shown in FIG. 5B, the free end 306 terminates in a leading face 310 that is preferably curved in accordance with a curvature defined by the peripheral wall 284a or 284b of the receiving region 282. Additionally, in one embodiment, the cam body 256 includes a finger 312 projecting from the lower side 302 at the leading face 310. The finger 312 terminates in a head 314 that further defines a shelf 316. With this configuration, the finger 312 is sized to slide along the peripheral wall 284a or 284b in the receiving region 282, with the head 314, and in particular the shelf 316, engaging the ridge 286 as described below.

With continued reference to FIG. 5B, and in accordance with one embodiment, the cam body 256 forms first and second internal bores 318, 320, extending from the bottom side 302. The first bore 318 is formed in the fixed end 304, and is sized to rotatably receive one of the pins 262 upon final assembly. In this regard, and as shown in FIG. 5A, the first bore 318 can extend through the top side 300 of the cam body 356; alternatively, the first bore 318 can be closed relative to the top side 300. The second bore 320 is formed at the free end 306, extending from the bottom side 302. The second bore 320 is sized to receive the spring member 258 as well as one of the bearing members 260 upon final assembly.

The spring member 258 is preferably a closed cell foam material, such as polyurethane, and is sized to nest within the second bore 320 of the cam body 356. In one embodiment, the spring member 258 is wedge-shaped, and defines first and second engagement surfaces 322, 324. The first engagement surface 322 is adapted to abut the bearing surface 289 of the bearing member 260. Conversely, the second engagement surface 324 is adapted to nest against an internal leading wall 326 (referenced generally in FIG. 5B), otherwise defining a portion of the second bore 320.

As with the previous embodiment, the cam body 256 is preferably adapted for assembly relative to a specific one of the guide faces 290 or 292. Thus, with respect to the orientation of FIG. 5A, a left cam body 256a and a right cam body 256b are preferably provided as mirrored constructions, but otherwise identical. With either configuration, assembly of the suture holding device 250 includes inserting the spring member 258 within the second bore 320 of a corresponding one of the cam bodies 256. The combination cam body 256/spring member 260 is then assembled to the base 252. In particular, the first bore 318 of the cam body 256 is aligned over the pin 262. Further, the bearing member 260 is aligned with the second bore 320. In particular, a relationship between the cam body 256, the spring member 258, and the bearing member 260 is such that the first engagement surface 322 of the spring member 258 nests against the bearing surface 284 of the bearing member 260; conversely, the second engagement surface 324 nests against the internal leading wall 326 of the cam body 256. Finally, the finger 312 is positioned along the peripheral wall 284a, with the shelf 316 abutting a bottom of the ridge 286. With this assembly, the head 314 nests between the ridge 286 and the bottom wall 288. The spring member 258 is slightly compressed between the internal leading wall 326 of the cam body 356 and the bearing surface 289 of the bearing member 260. As such, the spring member 258 biases the internal leading wall 326 away from the bearing member 260, effectively pivoting the cam body 256 about the pin 262 so that the toothed surface 308 contacts the corresponding guide face 290 or 292.

During use, a surgical suture (not shown) is secured to the suture holding device 250 in a manner highly similar to that previously described with respect to the suture holding device 20 (FIG. 1). In particular, the suture is positioned above the interface point between the toothed surface 308 of the cam body 256 and the guide face 290 or 292 of the corresponding guide body 254. The suture is then directed downwardly, and a slight rearward tension (e.g., away from the exit side 296) is applied, such that the suture slides between the cam body 256 and the guide body 254. The suture is then released, with friction between the suture and the toothed surface 308, as well as a bias provided by the spring member 254, causing the cam body 256 to pivot about the corresponding pin 262 such that the suture is secured between the toothed surface 308 and the corresponding guide face 290 or 292. The suture can subsequently be released by tensioning the suture away from the exit side 296 of the relevant guide face 290 or 292 while simultaneously lifting the suture relative to the cam body 256/guide body 254.

Figure 6A:
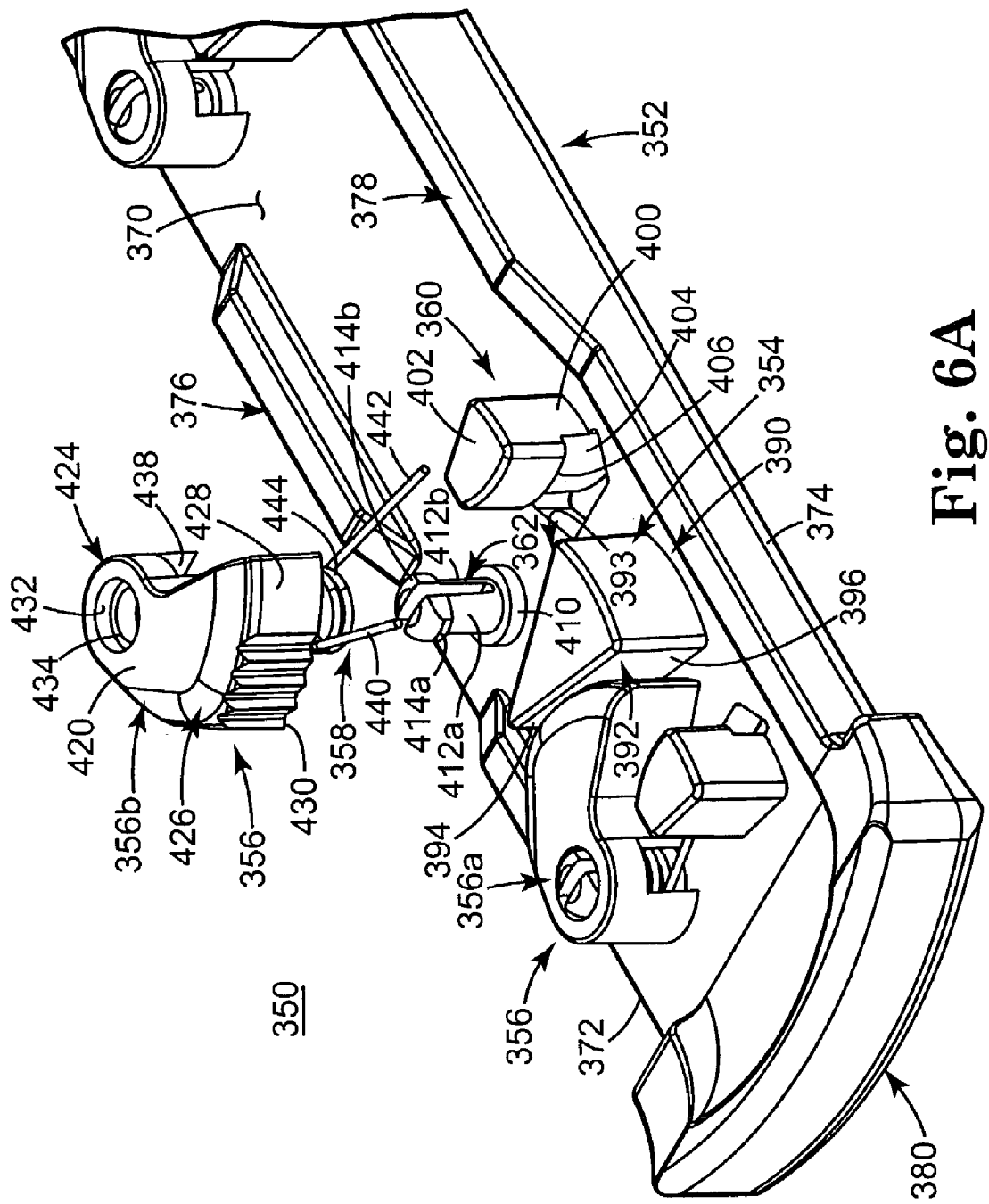
FIG. 6A is a top, exploded view of an alternative embodiment suture holding device.
Figure 6B:
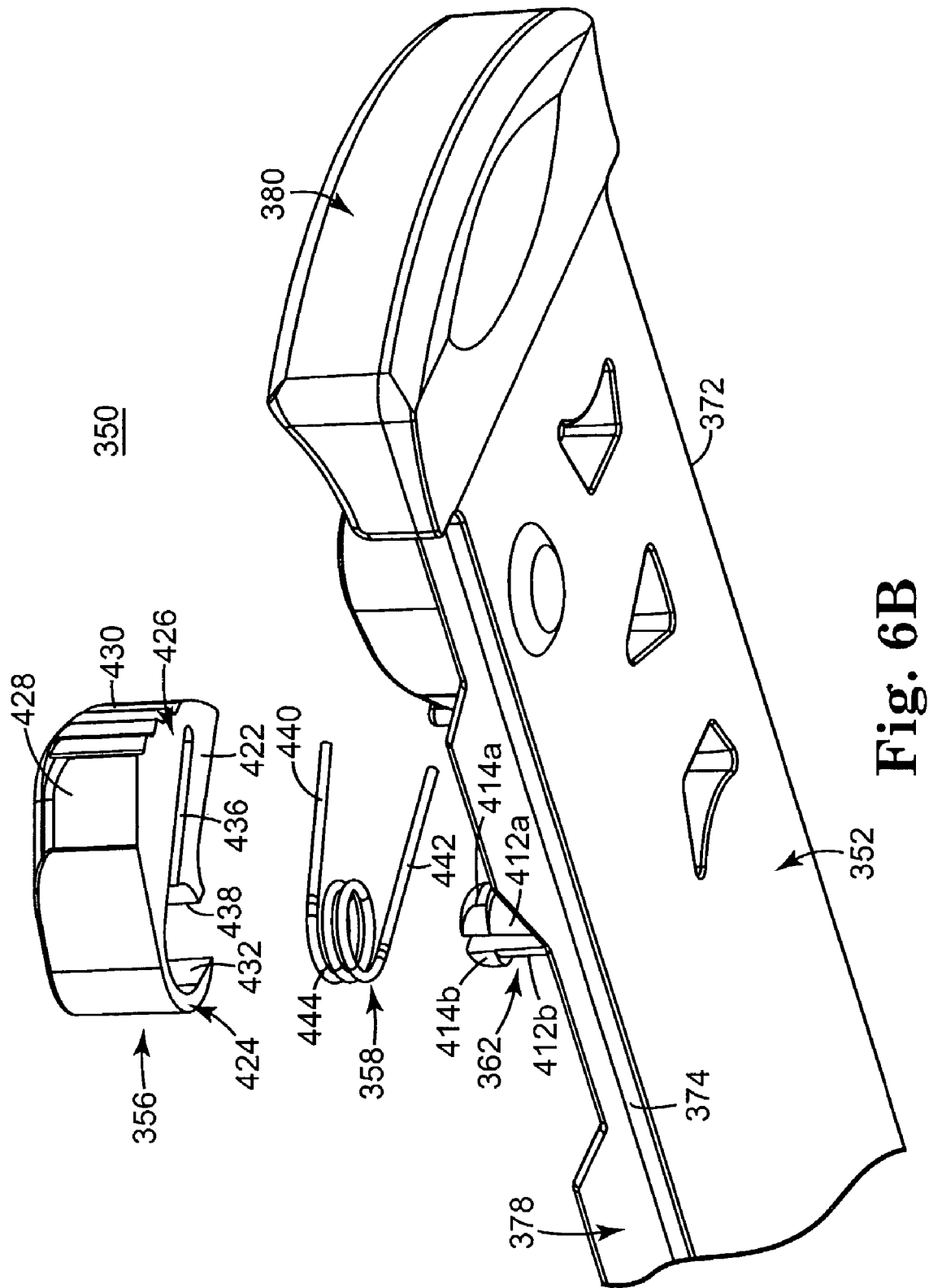
FIG. 6B is a bottom exploded view of the device of FIG. 6A.

Yet another alternative embodiment suture holding device 350 is shown in FIGS. 6A and 6B. The holding device 350 is similar to previous embodiments, and includes a base 352, at least one guide body 354, and at least one cam body 356. A spring member 358 is provided for each cam body 356, as are a bearing member 360 and a pin 362. As with previous embodiments, the cam body 356 is pivotally assembled to the base 352 via the pin 362. The spring member 358, via the bearing member 360, biases the cam body 356 toward the guide body 354.

The base 352 is similar to previous embodiments, and includes a top side 370, a front edge 372, and a back edge 374. Various other components of the holding device 350 are assembled to and/or project from the top side 370. For example, in one preferred embodiment, the one or more cam bodies 356, bearing member(s) 360, and pin(s) 362 are formed as molded projections relative to the top side 370. Additional features similar to those previously described, such as a first shoulder 376, a second shoulder 378, and/or a handle 380 can also be provided.

As with previous embodiments, the guide body 354 is positioned along the top side 370 within a suture receiving zone 390 (referenced generally in FIG. 6A). In this regard, the guide body 354 is wedge-shaped, defining opposing guide faces 392, 393 (with the guide face 393 hidden in FIG. 6A, but reference generally). Each of the guide faces 392, 393 defines an entrance side 394 and an exit side 396. The guide body 354 is positioned such that the entrance side 394 is adjacent the front edge 372, whereas the exit side 396 is adjacent the back edge 374.

Each of the bearing members 360 includes a lower segment 400 extending from the top side 370, and a head 402 extending from the lower region 400. The lower region 400 forms a contact surface 404. Further, extension of the head 402 relative to the lower region 400 defines a ledge 406 adjacent the contact surface 404.

With the embodiment of FIGS. 6A and 6B, the pin 362 is preferably a generally cylindrically-shaped body, and includes a platform 410 and opposing legs 412a, 412b. The platform 410 is attached to the top side 370, and defines a circular perimeter. The legs 412a, 412b are connected to one another at the platform 410, each forming a rib 414a, 414b opposite the platform 410. The legs 412a, 412b are compressible toward one another, but exhibit an inherent bias toward a relaxed position in which a spacing is established between the ribs 414a, 414b. Alternatively, other constructions for the pin 362 are acceptable.

The cam body 356 is similar to previous embodiments, and includes an upper side 420 (FIG. 6A), a lower side 422 (FIG. 6B), a fixed end 424, and a free end 426. The free end 426 terminates in a leading face 428 along which a toothed surface 430 is defined.

An internal bore 432 is formed at the fixed end 424, extending from the lower side 422 to the upper side 420. The internal bore 432 is sized to receive the pin 362 along with a portion of the spring member 358 as described in greater detail below. In one preferred embodiment, a diameter of the internal bore 432 is increased adjacent the upper side 420, such that a circumferential flange 434 (best shown in FIG. 6A) is formed along the internal bore 432. The circumferential flange 434 is adapted to receive the ribs 414a, 414b provided by a corresponding one of the pins 362. In addition to the circumferential flange 434, the cam body 356 further forms, in one embodiment, a groove 436 (best shown in FIG. 6B) and a passage 438, both of which are open to the internal bore 432. The groove 436 is sized to receive a corresponding portion of the spring member 358, whereas the passage 438 is adapted to allow extension of a portion of the spring member 358 from the cam body 356 to the bearing member 360 upon final assembly.

With the embodiment of FIGS. 6A and 6B, the spring member 358 is a coiled spring having first and second arms 440, 442 extending from a coil 444. The coil 444 is adapted to bias the first and second arms 440, 442 away from one another to the orientation shown in FIG. 6B. That is to say, the coil 444 establishes a lateral, relaxed state spacing between the arms 440, 442. The arms 440, 442 can be compressed toward one another when a spring force of the coil 444 is overcome. However, the coil 444 maintains a bias between the arms 440, 442 toward the relaxed state lateral spacing.

As with previous embodiments, a pair of left and right cam bodies (referenced as 356a and 356b in FIG. 6A) are preferably provided for each securement zone 390. The left and right cam bodies 356a, 356b mirror one another in design, but are otherwise preferably identical. Regardless, assembly of respective ones of the cam bodies 356 and spring members 358 within one of the securement zones 390 include capturing the spring member 358 relative to the cam body 356. In particular, the spring member 358 is oriented such that the first arm 440 is above the second arm 442. The coil 444 is inserted within the internal bore 432 via the bottom side 422, with the first arm 440 being received within the groove 436. The assembled cam body 356/spring member 358 is then assembled to the base 352. In particular, the internal bore 432, and thus the retained coil 444, is aligned over the pin 362. The cam body 356/spring member 358 is then forced toward the top side 420 of the base 352, with the legs 412a, 412b of the pin 362 being forced toward one another such that the opposing ribs 414a, 414b slide within the internal bore 432. Once the ribs 414a, 414b pass beyond the circumferential flange 434, the legs 412a, 412b are internally biased away from one another (or back toward a relaxed state spacing), such that the ribs 414a, 414b engage the circumferential flange 434, thus capturing the cam body 356 relative to the base 352. The second arm 442 of the spring member 358 extends from the cam body 356, via the passage 438, and nests against the contact surface 404 of the bearing member 360. In this regard, the first arm 440 is fixed relative to the cam body 356, such that a spring force is created by the coil 444 and imparted onto the second arm 432, causing the second arm 442 to lodge against the ledge 406 of the bearing member 360.

During use, the cam body 356 can pivot about the pin 362. In this regard, the platform 410 contacts an internal cam body wall (unnumbered), otherwise defining the internal bore 432 of the cam body 456, thereby guiding the cam body 356 through a desired pivoting or rotational motion. Further, the spring member 358 biases the toothed surface 430 against the corresponding guide face 392 or 393 of the guide body 354. In particular, a spring force generated by the coil 444 is applied to the cam body 356 via the second arm 442 bearing against the contact surface 404 of the bearing member 360, and the first arm 440 bearing against the cam body 356.

The holding device 350 is used to selectively secure a surgical suture (not shown) in a manner highly similar to that previously described for other embodiments. In particular, the surgical suture is positioned above the interface between the toothed surface 430 and the corresponding guide face 392 or 393 of the guide body 354. The suture is pressed downwardly in conjunction with a slight rearward tension (e.g., the suture is tensioned away from the exit side 396 of the guide face 392 or 393), causing the toothed surface 430 to slightly pivot away from the guide face 392 or 393. The suture can then slide between the toothed surface 430 and the guide face 392 or 393. Once released, friction between the suture and the toothed surface 430, in combination with the spring tension generated by the spring member 358, causes the toothed surface 430 to press the suture against the guide face 392 or 393 such that the suture is secured. Subsequently, the suture can be released by tensioning the suture away from the exit side 396 of the guide face 392 or 393, and pulling the suture upwardly, away from the guide body 354/cam body 356.

The suture holding device of the present invention provides a marked improvement over previous designs. The cam body, and in particular the toothed surface, is consistently positioned and pivoted relative to the guide face by a pin such that a surgical suture is quickly and consistently secured and released. Structural components that might otherwise impede a desired extension orientation of the suture relative to the holding device are eliminated, and users are afforded the ability to easily view all components and their positioning relative to one or more sutures retained thereby.

Although the present invention has been described with reference to preferred embodiments, workers skilled in the art will recognize that changes can be made in form and detail without departing from the spirit and scope of the present invention. For example, while the various embodiments have made reference to one construction whereby a plurality of guide bodies and a plurality of cam bodies are provided, alternative configurations in accordance with the present invention can employ on a single guide body for any of the disclosed embodiments. Similarly, the guide body need not be wedge-shaped, and only a single cam body (and other relevant components) can be assembled relative to the guide body.

What is claimed is:

1. A device for holding a surgical suture, the device comprising:
   a base having a top side, a front edge, and a back edge;
   a first guide body projecting from the top side, the guide body forming a wedge defining opposing first and second guide faces each having an entrance side adjacent the front edge and an exit side adjacent the back edge;
   a first cam body pivotally mounted to the top side, the first cam body forming a toothed surface positioned to secure a surgical suture between the toothed surface and the first guide face when the suture is tensioned in a first direction, and release the surgical suture when the suture is tensioned in an opposite direction;
   a first bearing member;
   a first spring member positioned between the first cam body and the first bearing member such that the first spring member biases the toothed surface toward the first guide face;
   a second cam body pivotally mounted to the top side forming a toothed surface positioned to selectively secure a surgical suture against the second guide face;
   a second bearing member; and
   a second spring member positioned between the second cam body and the second bearing member for biasing the toothed surface of the second cam body toward the second guide face;
   wherein the device is characterized by an absence of a channel formed at the front edge opposite the entrance side of the first guide body, and further characterized by the interface being open opposite the top side.

2. The device of claim 1, wherein the device is characterized by an absence of a channel formed at the back edge opposite the exit side of the guide body.

3. The device of claim 1, wherein an engagement region is defined along a length of the first guide face, the device further characterized by an absence of a rigidly defined channel in the engagement region.

4. The device of claim 1, wherein:
   a first shoulder projecting from the top side along at least a portion of the front edge.

5. The device of claim 4, further comprising:
   a second shoulder projecting from the top side along at least a portion of the back edge opposite the exit side of the guide body, the second shoulder defining a continuous height.

6. The device of claim 1, further comprising:
   a second guide body projecting from the top side and spaced from the first guide body, the second guide body defining a guide face; and
   a third cam body pivotally mounted to the top side and defining a toothed surface positioned to selectively secure a surgical suture against the guide face of the second guide body;
   wherein a spacing between the first and third cam bodies is less than a spacing between the first and second guide bodies, and further wherein at least a substantial portion of the top side is exposed between the first and third cam bodies.

7. The device of claim 1, wherein a wedge defines an apex, a back wall opposite the apex, and an upper surface, and further wherein at least a portion of the upper surface curves toward the top side of the base from the apex to the back wall.

8. The device of claim 7, wherein each of the guide surfaces taper in height from the entrance side to the exit side.

9. The device of claim 1, wherein the guide body defines an upper surface and a transition region between the upper surface and the first guide face, and further wherein at least a portion of the transition region is curved in transverse cross-section.

10. The device of claim 1, wherein the first cam body defines a top surface and a transition region between the top surface and the toothed face of the first cam body, and further wherein the transition region is curved in transverse cross-section.

11. The device of claim 1, wherein the first spring member is integrally formed with the first cam body.

12. The device of claim 11, wherein the first spring member is an arm extending from the first cam body.

13. The device of claim 12, wherein the toothed surface of the first cam body is formed on a free end of the first cam body opposite a fixed end, and further wherein the arm extends from the fixed end.

14. The device of claim 13, wherein the arm extends from the first cam body to a leading section defining a contact surface, and further wherein the contact surface abuts the first bearing member.

15. The device of claim 14, wherein the first bearing member defines an intermediate ledge adapted to receive the leading section of the arm.

16. The device of claim 1, wherein the first cam body defines an upper surface, a lower surface, and an internal bore formed through the lower surface, and further wherein the first spring member is adapted to be received within the bore.

17. The device of claim 16, wherein the first spring member is a foam material.

18. The device of claim 17, wherein the first bearing member is a tab projecting from the top side of the base, and further wherein the first spring member and the tab are received within the internal bore.

19. The device of claim 18, wherein the internal bore is defined in part by an internal leading wall, and further wherein the first spring member is compressed between the tab and the internal leading wall.

20. The device of claim 16, wherein the first spring member is a coil spring including a first arm nested within the first cam body and a second arm extending from the first cam body to the first bearing member.

21. The device of claim 1, further comprising:
a pin extending from the top side of the base;
wherein the first cam body is rotatably mounted onto the pin.

22. The device of claim 1 in combination with a surgical frame, wherein the base is an elongated body adapted to be slidably inserted within a recess of a surgical frame.

23. The device of claim 22, wherein the base further defines a leading side and a trailing side, and is configured such that the trailing side extends from the surgical frame upon assembly thereto, the device further comprising:
a handle formed at the trailing side of the base.

24. The device of claim 1, wherein the first and second cam bodies comprise a first pair of cam bodies, the device further comprising:
a second wedge-shaped guide body projecting from the top side of the base; and
a second pair of cam bodies each having a toothed surface positioned to selectively secure a surgical suture against a respective guide face defined by the second guide body.

25. The device of claim 24, further comprising:
a first shoulder projecting from the top side of the base at the first edge opposite at least the first and second guide bodies; and
a second shoulder projecting from the top side of the base at the back edge thereof opposite at least the first and second guide bodies.

26. The device of claim 25, wherein a maximum height of the second wall is greater than a maximum height of the first wall.

27. A device for holding a surgical suture, the device comprising:
a base having a top side; and
a plurality of spaced, suture securement zones defined along the top side including a first zone and a second zone, each zone including:
a guide body projecting from the top side and defining a guide face having an entrance side and an exit side;
first a cam body pivotally mounted to the top side, the cam body forming a toothed surface and adapted to maintain a spring member, wherein the toothed surface is positioned to secure a surgical suture between the toothed surface and the guide face when the suture is tensioned in a first direction, and release the surgical suture when the suture is tensioned in an opposite direction;
a bearing member positioned to contact a portion of the spring member such that the spring member biases the toothed surface toward the guide face; and
a second cam body pivotally mounted to the top side for selectively maintaining a suture against the guide body;
wherein a spacing between the first cam body of the first suture securement zone and the second cam body of the second securement zone is less than a spacing between the guide body of the first suture securement zone and the guide body of the second suture securement zone, and further wherein at least a substantial portion of the top side is exposed between the first cam body of the first suture securement zone and the second cam body of the second suture securement zone.

28. The device of claim 27, wherein the spring member is an arm integrally formed with the cam body.

29. The device of claim 27, wherein the spring member is retained within an internal bore formed by the cam body.

30. The device of claim 27, further comprising:
a pin extending from the top side of the base;
wherein the cam body is rotatably mounted to the pin.

31. A method of holding a surgical suture, the method comprising:
providing a suture holding device including a base, a guide body, a cam body, a bearing member, and a spring member, the guide body projecting from a top side of the base and defining a guide face having an entrance side and an exit side, the cam body being pivotally mounted to the top side and forming a toothed surface, the spring member being disposed between the cam body and the bearing member for biasing the toothed surface toward the guide face, wherein an engagement region is defined relative to a length of the guide face and the device is characterized by an absence of a rigidly defined channel in the engagement region;
providing a surgical suture including a leading section, an intermediate section, and a trailing section;
positioning the intermediate section between the toothed surface and the guide face such that the leading section extends from the entrance side and the trailing section extends from the exit side; and
tensioning the leading section away from the entrance side such that the toothed surface frictionally locks the intermediate section against the guide face.

32. A device for holding a surgical suture, the device comprising:
a base having a top side, a front edge, and a back edge;
a guide body projecting from the top side, wherein the guide body is a wedge defining an apex, a back wall opposite the apex and having a width greater than a width of the apex, an upper surface, and a guide face having an entrance side at the apex and terminating in an exit side at the back wall, at least a portion of the upper surface curves toward the top side of the base from the apex to the back wall;
a cam body pivotally mounted to the top side, the cam body forming a toothed surface positioned to secure a surgical suture between the toothed surface and the guide face when the suture is tensioned in a first direction, and release the surgical suture when the suture is tensioned in an opposite direction;
a bearing member; and
a spring member positioned between the cam body and the bearing member such that the spring member biases the toothed surface toward the guide face;
wherein the device is characterized by an absence of a channel formed at the front edge opposite the entrance side of the guide body.

33. The device of claim 32, wherein the guide surface tapers in height from the entrance side to the exit side.

34. A device for holding a surgical suture, the device comprising:
a base having a top side, a front edge, and a back edge;
a first guide body projecting from the top side, the guide body defining a guide face having an entrance side adjacent the front edge and an exit side adjacent the back edge;

a first cam body pivotally mounted to the top side, the cam body forming a toothed surface positioned to secure a surgical suture at an interface between the toothed surface and the guide face when the suture is tensioned in a first direction, and release the surgical suture when the suture is tensioned in an opposite direction;

a bearing member; and a spring member positioned between the cam body and the bearing member, wherein the spring member biases the toothed surface into contact with the guide face, wherein the spring member is an arm integrally formed with and extending outwardly from the cam body, extension of the arm beyond the cam body including a curved torsion section;

wherein the device is characterized by an absence of a channel formed at the front edge opposite the entrance side of the guide body, and further characterized by the interface being open opposite the top side.

* * * * *